(12) United States Patent
Nilsson

(10) Patent No.: US 6,513,663 B1
(45) Date of Patent: Feb. 4, 2003

(54) POWDER FEEDING DEVICE

(75) Inventor: Lars-Gunnar Nilsson, Köping (SE)

(73) Assignee: Microdrug AG, Hergiswil (CH)

( * ) Notice: Subject to any disclaimer, the term of this patent is extended or adjusted under 35 U.S.C. 154(b) by 0 days.

(21) Appl. No.: 09/744,744

(22) PCT Filed: Jul. 8, 1999

(86) PCT No.: PCT/SE99/01243

§ 371 (c)(1),
(2), (4) Date: Jan. 29, 2001

(87) PCT Pub. No.: WO00/06236

PCT Pub. Date: Feb. 10, 2000

(30) Foreign Application Priority Data

Jul. 30, 1998 (SE) .............................................. 9802648

(51) Int. Cl.[7] ........................... B03C 7/00; A61M 15/00
(52) U.S. Cl. ..................... 209/5; 209/12.2; 209/127.1; 128/203.15; 128/203.21
(58) Field of Search ............................... 209/2, 4, 5, 7, 209/10, 11, 12.2, 127.1; 128/203.12, 203.15, 203.21

(56) References Cited

U.S. PATENT DOCUMENTS 5,655,523 A * 8/1997 Hodson et al. ............. 128/315
5,694,920 A * 12/1997 Abrams et al. ...... 128/203.12 X
5,875,776 A * 3/1999 Vaghefi ................. 128/203.15

* cited by examiner

Primary Examiner—Tuan N. Nguyen
(74) Attorney, Agent, or Firm—Young & Thompson

(57) ABSTRACT

The invention discloses a method and a device for de-agglomeration and electrostatic charging of a fine powder preferably intended for inhalation purposes. The electrostatic charging takes place by means of tribo, corona and/or inductive charging. The device according to the invention is particularly intended for being able to dose decomposed powder directly into the inspiration air for administering of, for instance, active pharmaceutical substances, alternatively provide a further dosing device with electrostatically charged de-agglomerated powder for an even more controlled dosing of the substance into the inspiration air. De-agglomeration preferably takes place in that two rotating brushes containing powder are touching each other. The bristles are rubbed against each other and thereby decompose the powder agglomerates. The rotation speed of the brushes is suitably optimized to achieve the best possible result for different powder substances. The design of the brushes is further optimized for the substances, which are to be de-agglomerated and electrostatically charged prior to an administering step.

14 Claims, 4 Drawing Sheets

POWDER FEEDING DEVICE

TECHNICAL FIELD

Figure 1:
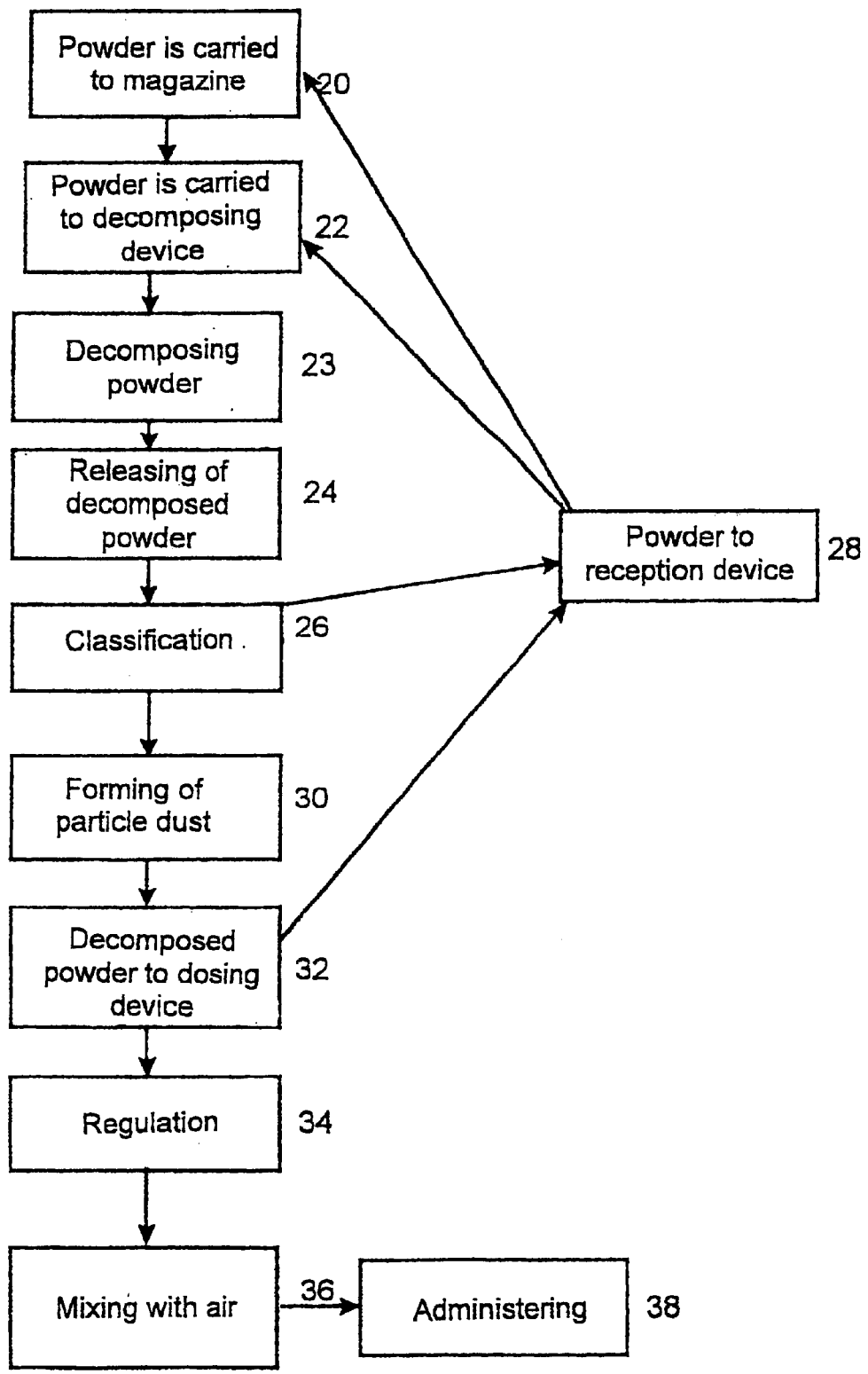
Figure 2:
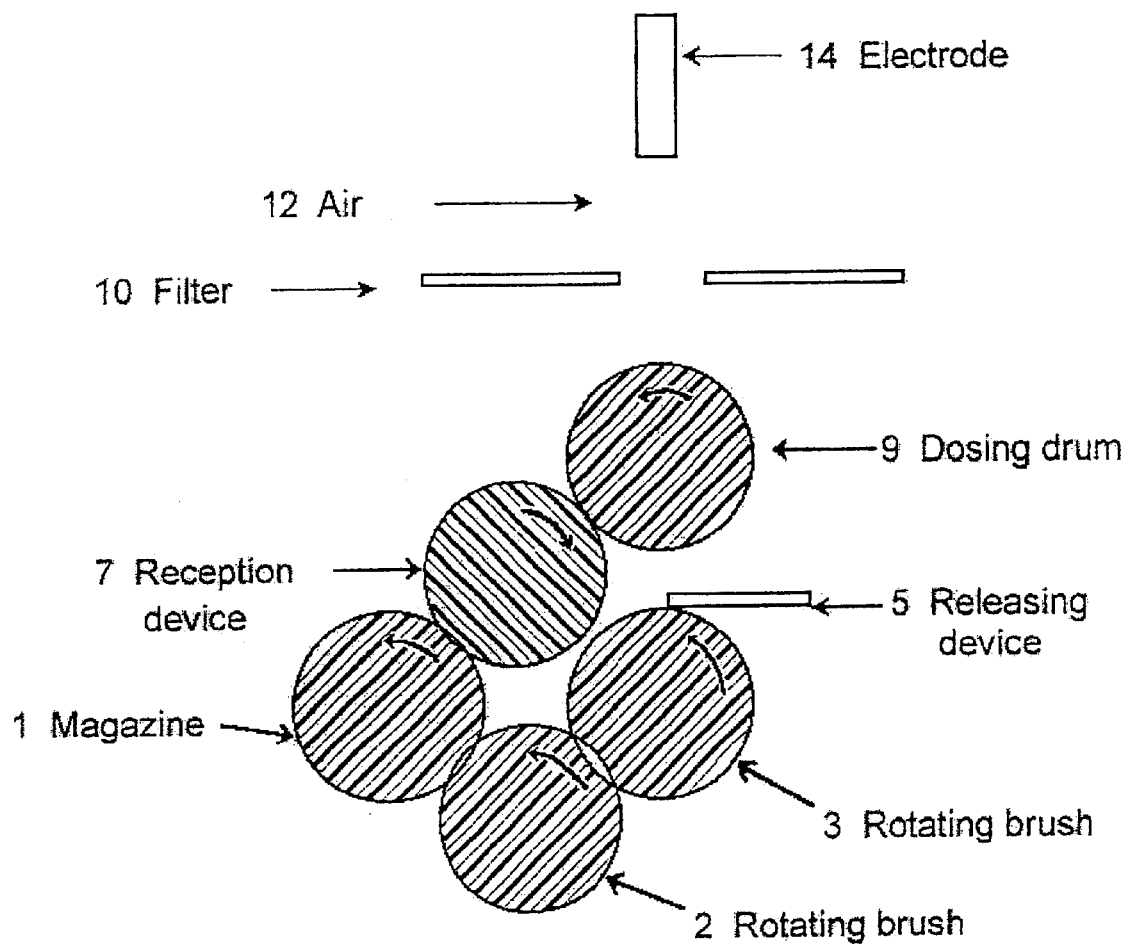

The present invention relates to a device for feeding, de-agglomeration and electrostatic charging of a pulverized powder for inhalation by means of stationary or portable devices, whereby powder refers to active pharmaceutical substances and mixtures and specially treated preparations intended to be administered via the respiratory tract.

BACKGROUND AND PRIOR ART

Administering of medical powders today is performed in numerous ways. Within health care more and more is focussed on the possibility of dosing powder directly to the lungs by means of an inhaler to obtain an effective, quick and patient-friendly administering.

For the medical powders, being administered by means of an inhaler, to land in the lungs, the powder should have a grain size of 1 to 6 μm. A larger grain size will stick in the mouth and throat and a smaller grain size accompanies the expiration.

Powder having a small grain size will have a strong tendency of agglomerating, i.e. to get conglomerated. In the inhalers which are used today a large extent of the active substance is in the form of agglomerates when it is dosed and much powder therefore will stick in the upper respiratory tract. Different ways to de-agglomerate the powder have been developed and in most cases the inhalation air is utilized for decomposing the agglomerates.

It is also common to use carriers having a larger grain size onto which the fine powder is distributed. Upon inspiration the large grains will then stick in the oral cavity while the small grains are set free and proceed to the lungs. Certain manufacturers also use electrically driven propellers, piezo-vibrators and/or mechanical vibration to decompose the agglomerates. Thus, achieving a very large portion of individual particles in the inspiratory air is a very important factor for obtaining a high degree of effectiveness upon inhalation.

In the Swedish patent publication SE 504 458 a device for an inhaler is disclosed, which utilizes a rotating drum as dosing device together with an electric field, which document hereby is incorporated by reference.

DESCRIPTION OF THE INVENTION

The present invention relates to a device for feeding, de-agglomeration and electrostatic charging of a fine powder, especially intended for inhalation purposes. The electrostatic charging takes place by means of tribo-, corona- and/or induction-charging. Charging of the powder is from now on referring to an electrostatic charging according to any of the mentioned ways or a combination of those. Particularly the device according to the present invention is used for dosing powder directly to the inspiratory air, alternatively providing a dosing device with electrostatically charged de-agglomerated powder for a more controlled dosing to the inspiratory air, alternatively application to a carrier for further preparation and introduction to an inhaler or other device, e.g., a piece of plaster or the like.

The de-agglomeration takes place in that two rotating brushes containing powder are touching each other. The bristles of the brushes are pinched and scraped toward each other and thereby decomposing the powder agglomerates. At the same time also an electrostatic charging of the powder may take place. The rotation speed of the brushes is optimized to achieve optimal results for different powder substances. The design of the brushes is preferably optimized for the substances to be de-agglomerated and electrostatically charged.

The choice of material then is adapted to the function the brushes are intended to have. If anti-static brushes are used, the main function is to decompose the agglomerates, while if another material is used, as for instance nylon, also a more pronounced electrostatic charging of the powder takes place.

As it is in practice impossible to obtain a complete de-agglomeration within the brushes, the dust delivered from the flipping device will contain a small amount of agglomerates. To have these agglomerates not to be integral in the powder to be dosed a separation must take place. This is arranged in a classification device, where a flipping takes place in the direction towards a reception device and where an electric field is present perpendicular to the direction of flipping. The kinetic energy, which is essentially larger for the agglomerates, will then convey the large particles to the reception device, while the small individual particles will be attracted to a dosing drum by means of the electric field. In this way only the individual particles will in practice be utilized for dosing.

The invention is defined by the independent claims 1 and 5 and different embodiments are defined by the dependent claims 2–4 and 6–14, respectively.

BRIEF DESCRIPTION OF THE DRAWINGS

The invention will be described in the form of a preferred illustrative embodiment and by means of the attached drawings wherein like reference numbers indicate like or corresponding elements and wherein:

FIG. 1 illustrates a flow chart of the path of powder through a device/an inhaler according to the present invention;

FIG. 2 illustrates a principal sketch of the feeding device in an illustrative embodiment for operation according to FIG. 1;

FIG. 3 illustrates another embodiment of the feeding device according to the present invention; and FIG. 4 further illustrates an embodiment of the feeding device according to the present invention.

DESCRIPTION OF AN ILLUSTRATIVE EMBODIMENT

Substances at first hand intended to be prepared are medical powders, but also other powders where an exact dosing of small quantities is needed may be considered. From now on in connection with the description of an illustrative embodiment powder will be used as a common word for all types of substances or preparations of substances, which shall be prepared.

FIG. 1 describes a method according to the present invention by illustrating in a schematic way the path of the powder through a dosing device according to FIG. 2. The powder is stored in a magazine 1. From the magazine, according to step 22, it is further fed to a decomposition device for de-agglomeration by means of a suitable device, e.g. in the form of a rotating plastic film or a brush. Superfluous powder is automatically brought back to the magazine 1 when the first brush 2 of the decomposition device is not able to receive more powder material. In this way a stable system is obtained, which maintains the powder feeding balance and thereby a possibility of even dosing will be obtained.

The de-agglomeration, which occurs in next step 23, takes place by smashing or decomposing the agglomerates by a suitably adapted device, which as was mentioned above, consists of two brushes in contact with each other according to the illustrative embodiment of the present invention. The powder is then, in step 24, released from the second brush 3 of the decomposition device in that it will, by means of a releasing member 5, be launched or flipped out from the second brush 3 in a way such that a dust cloud is formed. The dust cloud at this time consists to a larger part of individual particles, but an amount of agglomerates remains. To obtain a de-agglomeration as complete as possible a classification takes place in the next step 26.

Utilizing kinetic energy and an electric field for separating individual particles from agglomerated particles performs the classification, in step 26. For this to take place the powder particles must get a high velocity and be electrostatically charged when they leave the releasing device 5. The powder agglomerates being of relatively large size will have a high energy of motion and these agglomerates therefore will proceed straight ahead. The small particles having a low energy of motion will more easily be able to be influenced by an electric field and change their direction of motion. Therefore an electric field is applied, the direction of which preferably being perpendicular to the direction of the motion the particles will obtain at the release from the brush 3.

The powder agglomerates travelling straight ahead will be taken care of by a reception means 7 for further conveying back to the magazine 1 or to the decomposition means. The individual particles forming a dust cloud are carried by the electric field, in a transfer step 32, to a dosing drum 9 for further preparation.

Figure 3:
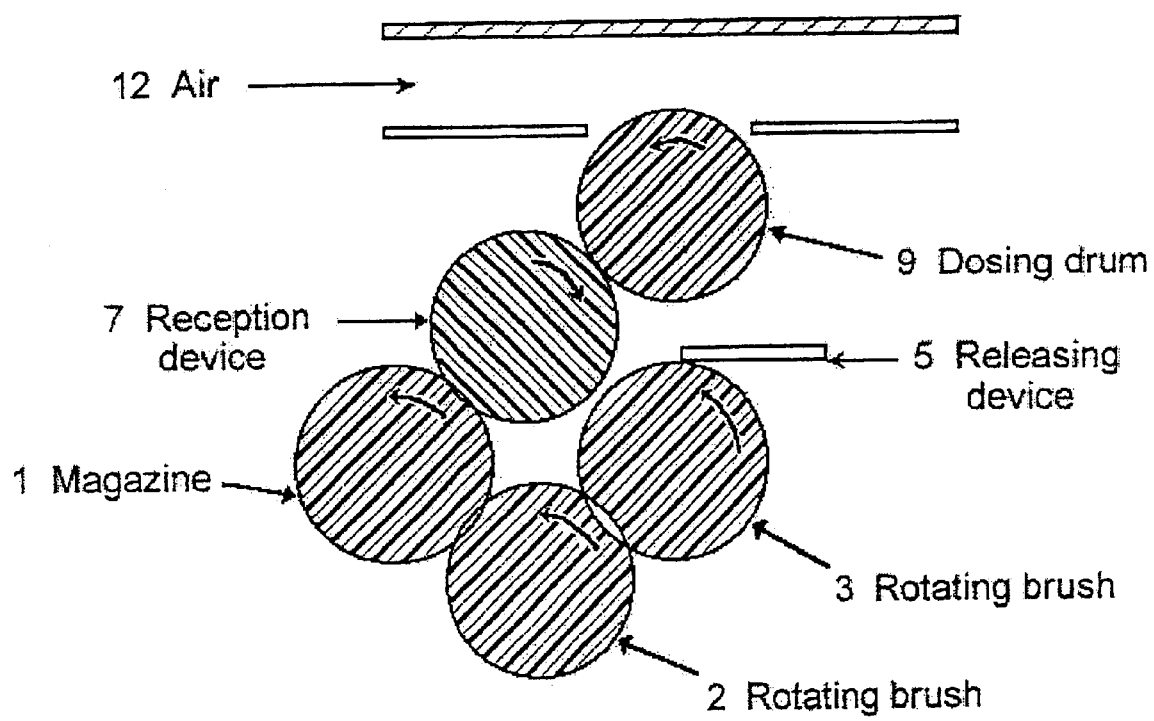
Figure 4:
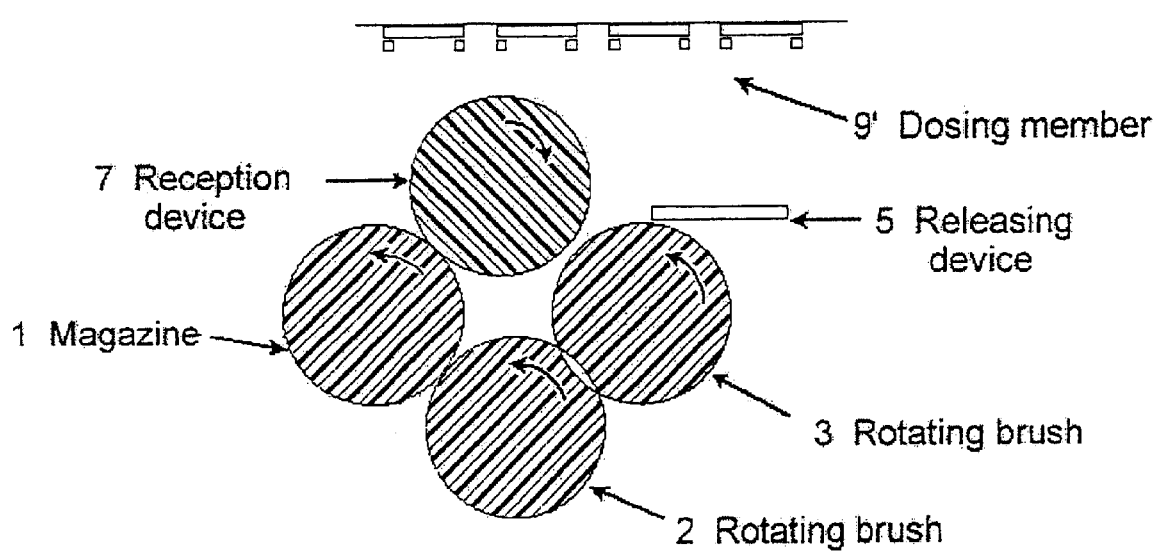

From the dosing drum 9 in the transfer step 32, dosing of powder to an air-stream takes place by means of an attracting electrode 14 or blowing off. The regulation of dosed amount of powder to the air, for instance, takes place by in a regulation step 34 varying a voltage and/or utilizing an electronically controlled filter 10. The dosing drum 9 is continuously cleaned from powder after that the dosing has taken place by its communication with the reception device 7. The powder which in this way is removed will be brought back via the reception device 7 to the rotating brushes 2 and 3 or the magazine 1, for instance by a further releasing device (not shown) corresponding to the device 5.

The result of the dosing, in step 36, will be an air flow, which contains a regulated amount of powder in the form of individual particles, which is a prerequisite to upon inhalation obtain a high efficiency for medical powders in the administering according to step 38.

An illustrative embodiment of the invention is disclosed in FIG. 2. The magazine 1 is preferably round and contains, in the illustrative embodiment, a slowly rotating thin disc of plastics or a brush, which when it passes a bump in the magazine compartment, flips powder in the direction towards a first conveying and decomposing brush (decomposing means) 2, such that it all the time has the same filling of powder. The magazine preferably is airtight and in communication with a compartment, which contains a moisture absorbing substance. In a further embodiment of the device an electric heating takes place to keep control of the climate within the apparatus.

The decomposition within the illustrative embodiment takes place by means of rotating brushes 2 and 3, whereby design and selection of material is adapted to the characteristics of the powder. In another embodiment also other means than rotating brushes would be used. The rotational speed and the direction of rotation act on the powder to a high degree, and too high a speed can result in tendencies of melting and deposition within the apparatus.

The selection of material is important for a correct electrostatic charging of the powder to be obtained and an important part in the grading therefore is where the material is to be found in the tribo-electric series. In many cases is it also necessary to use conducting materials if it is desirable to avoid electrostatic charging. The following table illustrates the grading of some materials in the tribo-electric series.

| Tribo-electric series |
|---|
| Positively charged |
| Glass |
| Nylon |
| Styrene |
| Rubber |
| Polyetene |
| PVC |
| Teflon |
| Negatively charged |

Further relating to electric characteristics the materials may be divided into three groups:

(1) Insulating materials, which are applicable for electrostatic charging, for instance by means of tribo-charging.

(2) Semi-conducting materials, which are not applicable for electrostatic charging, but being appropriate for certain portions of the apparatus, which should be set at a voltage potential.

(3) Conducting material as such necessary to use for avoiding electrostatic charging and to obtain a proper grounding.

The distance between the brushes is adjusted such that an optimal de-agglomeration is obtained. Normally it is preferable that the bristles of the brushes enters into each other between 0 and 3 mm. Just at the contact between the bristles agglomerated powder is rubbed to decompose and the brushes will in this way mainly contain individual particles.

To release the powder from the brush a releasing device 5 is used. An adequate releasing device, for instance, is a disc of appropriate material, which upon the rotation of the brush bends the bristles such that the powder is flipped when the bristles get straight again. A further alternative is to have an additional brush instead of the disc in the releasing device.

The dust from the rotating brush 3 in the releasing device goes out into a compartment where a classification takes place, i.e. a separation such that remaining agglomerated powder material can be brought back to the magazine 1 or to the decomposition means. This portion of the powder is carried to the reception device in form of an additional rotating brush 7, while the decomposed powder as dust, which constitute individual particles, goes further to dosing by being distributed over a dosing drum 9.

The dosing itself takes place in that an attracting electrode with an appropriate voltage attracts the powder grains from the dosing drum 9. The potential of the attracting electrode is possible to vary between wide limits with an applied voltage normally between about 500 and 3000 volts. A flow of air, the inspiratory air, will drag away the small powder grains before those reach the attraction electrode. The amount of dosed powder can be governed by connecting and disconnecting the voltage to the attraction electrode. Alternatively the dosing may be regulated in that an electronic filter is inserted between the dosing drum and the attraction electrode. A further alternative is that the airflow directly releases powder from the dosing drum, which is then positioned higher up in the device in direct contact with the airflow, which is illustrated in FIG. 3. The regulation in this case takes place by varying the electric field in the classification process corresponding to the step 26 of FIG. 1.

A normal method in connection to inhaler is that they are loaded with powder in the form of capsules. Disposable inhalers are loaded with one capsule while multi-use inhalers often are loaded with a strip containing several capsules. A further alternative therefore is that the dosing drum 9 is replaced by a powder dispenser (capsules) 9' which may be separate or be part of a strip in a way illustrated generally in FIG. 4. In this way the described feeding and dosing device advantageously may be used to in a simple way fill the capsules with an exact amount of powder, which according to the invention only consists of individual particles suitable for administering by inhalation. The device according to FIG. 4 presents as for the rest corresponding elements as in FIGS. 2 and 3.

The entire dosing apparatus then is designed such that no compartment is created where the powder may build up or rest. The selection of material here is also important for minimizing deposits. This further takes place in that walls and other parts are given the same or a higher potential and with same polarity as the electrostatically charged powder to create a repulse of the powder.

The method and the device have been disclosed by means of an illustrative embodiment, which however shall not be seen as limiting the scope of the invention, which instead is set forth by the appended claims.

What is claimed is:

1. A device for feeding, decomposing and electrostatic charging of a powder intended for administering mainly by inhalation, characterized in that it comprises a magazine (1) for powder to be administered;

a first rotating means (2) in communication with the magazine (1)

a second rotating means (3) in communication with the first rotating means (2), whereby the first means and the second means form a de-agglomeration zone where present powder agglomerates are decomposed into individual powder particles suitable for administering;

a releasing means (5) for releasing decomposed powder from the second rotating means (3);

a third rotating means (7) for bringing agglomerates not decomposed back to the magazine (1) or to the first rotating means (2); and a dosing means (9) for reception of the decomposed powder for administering.

2. The device according to claim 1, characterized in that the de-agglomeration zone is constituted by a first and a second rotating brush (2,3), whereby bristles of the two brushes are brought in engagement with each other and in the communication between the bristles agglomerated powder will be rubbed to decompose and the second brush (3) will essentially contain individual powder particles.

3. The device according to claim 1, characterized in that an electrostatic charging of the powder takes place by means of tribo or corona or inductive charging or a combination of these by selection of an appropriate material in relation to the tribo-electric series and in relation to applied voltages in the releasing means (5).

4. The device according to claim 3, characterized in that the material of the device is selected such that at least one of tribo, corona and inductive charging of the powder will be governed by externally applied and controlled fields.

5. The device according to claim 1, characterized in that the magazine for the powder comprises a slowly rotating disc or brush, which when it passes a bump flips powder towards said first rotating means (2).

6. The device according to claim 1, further comprising a container for a dehydrant to obtain a controlled climate regarding level of moisture.

7. The device according to claim 1, further comprising an electrical heating device for control of climate in the feeding and decomposition compartments.

8. The device according to claim 1, characterized in that within the device a compartment is arranged for the ready-made powder in form of dust for later handling.

9. The device according to claim 1, characterized in that said device comprises walls made of a conducting or semi-conducting material having an electric potential of the same sign as the charged powder to minimize deposits.

10. The device according to claim 1, characterized in that the dosing means (9') is designed as a powder technical source in the form, for instance, of a strip for a later mounting in a separate inhalation device.

11. A method for feeding, decomposition and electrostatic charging of a powder intended for administering mainly by inhalation, characterized by the steps of:

decomposition of agglomerated powder into individual powder particles, which is achieved in that a first rotating means (2) and a second rotating means (3) are brought in engagement with each other, whereby the powder agglomerates, which are conveyed by the first rotating means is decomposed;

releasing of the decomposed powder from the second rotating means (3) by means of a releasing device (5);

separation of individual powder particles and remaining agglomerated powder by means of a classification device;

pick up of agglomerated powder by a reception device (7) for bringing that back to a magazine (1) or to the first rotating means (2);

transfer of the individual powder particles to a dosing drum 9; and dosing of the individual powder particles controlled by means of an electric field bringing decomposed powder particles from the dosing drum (9) into an airflow.

12. The method according to claims 11, characterized by the further step of a charging of the powder at the first and second rotating means (2 and 3) or at the releasing device (5) by selection of an appropriate material relative to the powder.

13. The method according to claim 11, characterized by the further step of air blowing off to further assist carrying out decomposed powder particles from the dosing drum (9) into the airflow (12).

14. The method according to claim 11, characterized in that the step of transferring individual powder particles to the dosing drum (9) is performed by means of an electrostatic field, obtained in that the dosing drum (9) is given an attracting electric potential in relation to the electric charge of the powder.

* * * * *